United States Patent
Sarrafzadeh et al.

(10) Patent No.: US 9,330,342 B2
(45) Date of Patent: May 3, 2016

(54) ON-BED MONITORING SYSTEM FOR RANGE OF MOTION EXERCISES WITH A PRESSURE SENSITIVE BED SHEET

(71) Applicant: The Regents of the University of California, Oakland, CA (US)

(72) Inventors: Majid Sarrafzadeh, Anaheim Hills, CA (US); Wenyao Xu, Rowland Heights, CA (US); Ming-Chun Huang, Sulver, CA (US); Jason J. Liu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 123 days.

(21) Appl. No.: 14/101,765

(22) Filed: Dec. 10, 2013

(65) Prior Publication Data
US 2014/0157911 A1 Jun. 12, 2014

Related U.S. Application Data

(60) Provisional application No. 61/735,408, filed on Dec. 10, 2012.

(51) Int. Cl.
*G06K 9/62* (2006.01)
*G06K 9/00* (2006.01)
(Continued)

(52) U.S. Cl.
CPC ............ *G06K 9/6248* (2013.01); *A61B 5/0013* (2013.01); *A61B 5/1036* (2013.01); *A61B 5/1128* (2013.01); *A61B 5/6892* (2013.01); *G06K 9/00342* (2013.01); *A61B 2505/07* (2013.01); *A61B 2505/09* (2013.01); *A61B 2562/0247* (2013.01)

(58) Field of Classification Search
CPC ......................... A63B 24/0003; G06K 9/00342
USPC ...................................... 73/862.041
See application file for complete search history.

(56) References Cited

U.S. PATENT DOCUMENTS

2009/0183312 A1 7/2009 Price et al.
2012/0190989 A1* 7/2012 Kaiser et al. .................. 600/476
(Continued)

FOREIGN PATENT DOCUMENTS

WO WO 2011066151 A1 * 6/2011

OTHER PUBLICATIONS

Liu et al., "On-Bed Monitoring for Range of Motion Exercises with a Pressure Sensitive Bedsheet", 2013 IEEE Conference on Body Sensor Networks (BSN), May 6-9, 2013.
(Continued)

*Primary Examiner* — Lisa Caputo
*Assistant Examiner* — Jamel Williams
(74) *Attorney, Agent, or Firm* — Foley & Lardner LLP; Cliff Z. Liu; Angela D. Murch

(57) ABSTRACT

A system includes a pressure sensitive material that provides an indication of applied pressure for multiple locations on the material, and an analysis device in communication with the pressure sensitive material. The analysis device receives the indication of applied pressure, determines, for each of multiple measurement periods, a pressure image from the indication of applied pressure such that a sequence of pressure images is determined, and constructs a manifold representing the sequence of pressure images.

20 Claims, 11 Drawing Sheets

(51) Int. Cl.
A61B 5/00 (2006.01)
A61B 5/103 (2006.01)
A61B 5/11 (2006.01)

(56) References Cited

U.S. PATENT DOCUMENTS

2012/0323501 A1* 12/2012 Sarrafzadeh et al. ............ 702/41
2013/0192071 A1* 8/2013 Esposito et al. .................... 33/6

OTHER PUBLICATIONS

Adami et al., "Detection of Movement in Bed Using Unobtrusive Load Cell Sensors," Transactions on Information Technology in Biomedicine, vol. 14, No. 2, pp. 481-490, Mar. 2010.
Delmarre et al., "3d Articulated Models and Multiview Tracking With Physical Forces," Computer Vision and Image Understanding, vol. 81, No. 3, pp. 328-357, 2001.
Fablet et al., "Automatic Detection and Tracking of Human Motion With a View-Based Representation," in Proceedings of the 7th European Conference on Computer Vision—Part I, 2002, pp. 476-491.
Foubert et al,. "Lying and Sitting Posture Recognition and Transition Detection Using a Pressure Sensor Array," in Medical Measurements and Applications Proceedings (MeMeA), 2012 IEEE International Symposium on, May 2012, pp. 1-6.
Harada et al., "Human Motion Tracking System Based on Skeleton and Surface Integration Model Using Pressure Sensors Distribution Bed," in Proc. Workshop on Human Motion, 2000, p. 99.
Hsia et al., "Bayesian Classification for Bed Posture Detection Based on Kurtosis and Skew-Ness Estimation," in e-health Networking, Applications and Services, HealthCom 10th International Conference, Jul. 2008, pp. 165-168.
Huang et al., "Smartglove for Upper Extremities Rehabilitative Gaming Assessment," in Proceedings of the 5th International Conference on Pervasive Technologies Related to Assistive Environments, 2012, pp. 20:1-20:4.
Jones et al., "Identifying Movement Onset Times for a Bed-Based Pressure Sensor Array," in Medical Measurement and Applications. IEEE International Workshop, Apr. 2006, pp. 111-114.

Jovanov et al., "A WBAN System for Ambulatory Monitoring of Physical Activity and Health Status: Applications and Challenges," in 27th Annual International Conference of the Engineering in Medicine and Biology Society, Jan. 2005, pp. 3810-3813.
Krebs et al., "Increasing Productivity and Quality of Care : Robot-Aided Neuro-Rehabilitation," Rehabilitation Research & Development, vol. 37, p. 639, Nov. 2000.
Li et al., "Dimensionality Reduction for Anomaly Detection in Electrocardiography: A Manifold Approach," in Wearable and Implantable Body Sensor Networks (BSN), 2012 Ninth International Conference, 2012, pp. 161-165.
Liu et al, "A Dense Pressure Sensitive Bedsheet Design for Unobtrusive Sleep Posture Monitoring," in IEEE International Conference on Pervasive Computing and Communications, Mar. 2013.
Nakajima et al., "Development of Real-Time Image Sequence Analysis for Evaluating Posture Change and Respiratory Rate of Subject in Bed," Physiological Measurement, vol. 22, No. 3, p. N21, 2001.
Saul et al., "Think Globally, fit Locally: Unsupervised Learning of Low Dimensional Manifolds," Journal of Machine Learning Research, vol. 4, pp. 119-155, Dec. 2003.
Tao et al., "Building a Visual Tracking System for Home-Based Rehabilitation," in in Proceedings of the 9th Chinese Automation and Computing Society Conference in the UK, 2003, pp. 343-348.
Xu et al, "eCushion: An eTextile Device for Sitting Posture Monitoring," in Body Sensor Networks (BSN), May 2011, pp. 194-199.
Xu et al., "Smart Insole: a Wearable System for Gait Analysis," in Proceedings of the 5th International Conference on Pervasive Technologies Related to Assistive Environments, ser. PETRA '12, 2012, pp. 18:1-18:4.
Yousefi et al., "Bed Posture Classification for Pressure Ulcer Prevention," in Engineering in Medicine and Biology Society, Sep. 2011, pp. 7175-7178.
Zhang et al., "Manifold Learning and Recognition of Human Activity Using Body-Area Sensors," in Machine Learning and Applications and Workshops (ICMLA), 10th International Conference, vol. 2, Dec. 2011, pp. 7-13.
Zhou H. et al., "Human Motion Tracking for Rehabilitation—A Survey," Biomedical Signal Proc. and Control, vol. 3, pp. 1-18, 2008.

* cited by examiner

Heel Slide

ON-BED MONITORING SYSTEM FOR RANGE OF MOTION EXERCISES WITH A PRESSURE SENSITIVE BED SHEET

CROSS-REFERENCE TO RELATED APPLICATION

This application claims the benefit of U.S. Provisional Application Ser. No. 61/735,408 filed on Dec. 10, 2012, the disclosure of which is incorporated herein by reference in its entirety.

BACKGROUND

Physical rehabilitation is a treatment program designed to help a subject to return to normal health following surgery or illness. In most cases, the aim is to improve muscular strength and range of motion. Physical rehabilitation is well recognized to provide lasting benefits. For example, Johns Hopkins Hospital has reported up to 22% reduction in ICU length of stays, and reductions in net cost, due to the early inclusion of physical rehabilitation programs in the recovery process.

Subjects undergoing physical rehabilitation follow an exercise regimen provided by a caregiver such as a physician or a physical therapist. Traditionally, rehabilitation programs are carried out in hospitals or therapy treatment centers, where trained caregivers provide instruction, monitor performance, and evaluate progress manually. As a result, the cost of rehabilitation can be high. Additionally, analysis of performance and recovery progress is subjective and may be difficult to quantify.

It would be beneficial for a subject to have the ability to perform physical therapy exercises in environments other than clinical settings, such as at home, without the need for a caregiver to be present. It would also be beneficial to provide for objective analysis of exercise performance and rehabilitation progress.

SUMMARY

In one aspect, a system includes a pressure sensitive material that provides an indication of applied pressure for multiple locations on the material, and an analysis device in communication with the pressure sensitive material. The analysis device receives the indication of applied pressure, determines, for each of multiple measurement periods, a pressure image from the indication of applied pressure such that a sequence of pressure images is determined, and constructs a manifold representing the sequence of pressure images. The analysis device may receive the indication of applied pressure continuously.

The pressure sensitive material may be an e-textile, such as, for example, a material constructed in multiple layers, including a first layer with conductive traces, a second layer of variable conductivity positioned next to the first layer, and a third layer with conductive traces positioned next to the second layer. The multiple locations on the material may be a plurality of intersections of the conductive traces of the first layer and the third layer, and at each intersection, the conductive traces of the first layer and the third layer cross at an angle with respect to each other, where the conductive traces of the first layer and the third layer are separately selectable to allow for measuring a conductance at each intersection. The indication of applied pressure may be the conductance measured at multiple intersections.

Constructing the manifold may include searching for the k nearest neighbors, perform a weighted reconstruction, and create a low dimensional embedding.

The indication of applied pressure may represent training data, and the manifold is a first manifold, and the analysis device is further configured to determine the similarity of a second manifold to the first manifold.

A manifold may represent a defined rehabilitation exercise, which may be, for example, one of leg lift, heel slide, lateral roll, head lift, and sit-up.

In another aspect, a method includes receiving a sequence of communications, each communication representing multiple pressure measurements made during a measurement period such that the sequence of communications provides information for a sequence of measurement periods; determining for each measurement period a pressure image from the multiple pressure measurements such that a set of pressure images are determined; and constructing a manifold from the set of pressure images.

Constructing the manifold may include searching for the k nearest neighbors; performing a weighted reconstruction; and creating a low dimensional embedding.

The information for the sequence of measurement periods may be training data, and the manifold is a first manifold, and the method includes determining a similarity between a second manifold and the first manifold.

Constructing the manifold may include pre-processing of the set of pressure images, dimension reduction using manifold learning, and exercise recognition using manifold matching.

The manifold may represent a defined rehabilitation exercise, which may be, for example, one of leg lift, heel slide, lateral roll, head lift, and sit-up.

In another aspect, the method is embodied as executable instructions in a non-transitory computer-readable storage medium.

In another aspect, a method includes receiving data representing conductance measurements from multiple pressure sensors; determining a sequence of pressure maps from at least a portion of the data; for each pressure map in the sequence of pressure maps, searching for the k nearest neighbors; performing a weighted reconstruction from the k nearest neighbors; and creating a low dimensional embedding of the weighted reconstruction. The low dimensional embedding may be embedding in a manifold The data may represent pressure between a subject and a surface measured at a plurality of points on the surface, and the low dimensional embedding represents a defined exercise performed by the subject on the surface.

The method may further include comparing the low dimensional embedding to a previously-created low dimensional embedding to identify the exercise. The method may also include determining a difference between an actual performance of the exercise and an expected performance of the exercise by way of the comparing.

The sequence of pressure maps may be a first sequence, and the method may include determining multiple sequences of pressure maps including the first sequence, and creating a low dimensional embedding based on the multiple sequences of pressure maps.

In another aspect, the method is embodied as executable instructions in a non-transitory computer-readable storage medium.

In another aspect, a non-transitory computer-readable storage medium includes instructions for determining at least one sequence of pressure maps from data representing pressure between an object and a surface measured at a plurality of times during an interval; pre-processing each pressure map of the at least one sequence of pressure maps, thereby generating at least one sequence of standardized and normalized pressure maps; and performing dimension reduction on the at least one sequence of standardized and normalized pressure maps using manifold learning.

The dimension reduction may result in the construction of a manifold representing a sequence of movements of the object.

The dimension reduction may result in the construction of a manifold representing an expected sequence of movements.

The manifold representing the expected sequence of movements may represent an expected performance of an exercise, and the instructions include instructions for comparing the manifold representing the expected sequence of movements to a manifold representing an actual sequence of movements to identify whether the actual sequence of movements represents a performance of the exercise.

The manifold representing the sequence of movements may be a first manifold and represents a record of performance of an exercise, and the instructions include instructions for comparing the first manifold to a second manifold to determine progress in performance of the exercise.

The system is convenient to set up, unobtrusive, and can be used for reliable, long term monitoring.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

Figure 1:
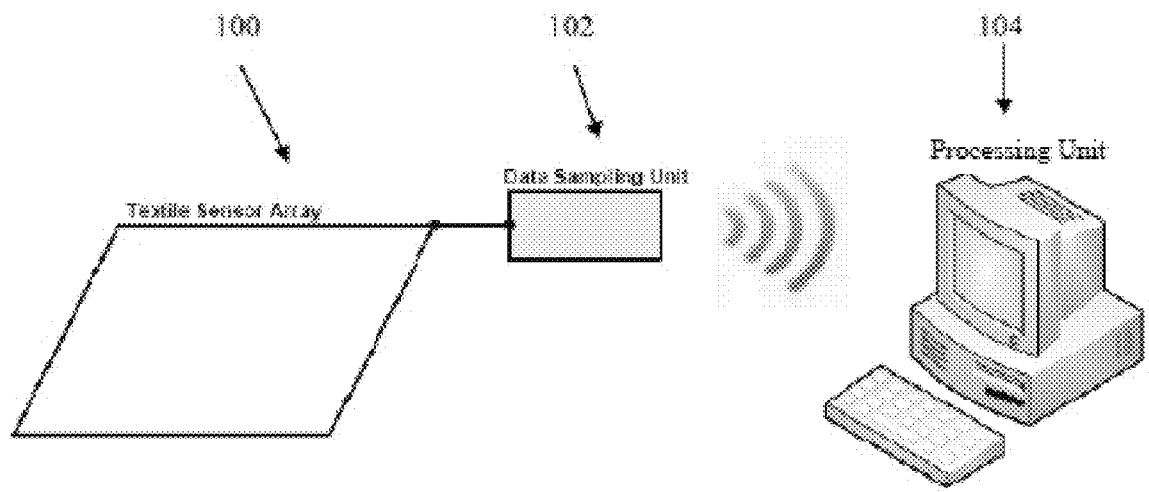
FIG. 1 shows an architecture of an exercise monitoring system, according to an embodiment of this disclosure.

This disclosure describes on-bed monitoring of rehabilitative exercises. Physical rehabilitation includes range of motion (ROM) exercises, such as: (a) passive ROM, where a physical therapist applies an external force to move a subject's body; (b) active assisted ROM, where the subject moves with assistance from a therapist; (c) active ROM, where the subject moves with no assistance; and (d) self-assisted ROM where the subject's motion is assisted by the subject (e.g., using the arms to extend the motion of the legs). Although the concepts of this disclosure may be used for all four types of ROM exercises, the concepts are particularly beneficial for active ROM and self-assisted ROM, which may be carried out by the subject alone, allowing for monitored exercising away from a care facility. Coherence to an exercise regimen may thus be monitored remotely as well as in a care facility.

Traditional rehabilitative monitoring of a subject is performed either by manual monitoring or camera-based monitoring, both of which tend to cause a monitored subject to feel uncomfortable. Additionally, camera-recorded images tend to reveal a subject's identity, and there are privacy concerns raised by recording. Because of this, recorded rehabilitative exercises are generally securely stored and are seldom published for research purposes. Therefore, most analysis is still manually performed by professional medical personnel, thereby limiting the scalability of studies. An advantage of monitoring using the bed sheet is that no camera is needed.

The concepts in this disclosure allow for monitoring a subject primarily, substantially, or only based on pressure images representing pressure of the subject's body across the bed sheet. A pressure image is determined from pressure data as provided by a sensor array in the bed sheet. A high density sensor array of the bed sheet provides for high resolution images of pressure distribution. The term 'image' in this context means an electronic representation of the pressure distribution, which may be, for example, displayed visually on an electronic display or other imaging device, printed, transmitted as a data stream, stored, and/or recalled.

Values for intensity of portions of a pressure image, and changes in a sequence of pressure images, indicate position of the subject and movement of the subject. High resolution images from many pressure sensors allow identification of positioning and movement of, for example, limbs and digits of the subject's body, without identification of the particular subject. In this way, gathered data can be freely distributed and systematically analyzed without implicating privacy issues.

Another advantage of the exercise monitoring system according to this disclosure, especially as compared with camera based monitoring devices, is inconspicuous deployment in a care facility, such that subjects may not be aware of the monitoring. Additionally, the disclosed system does not have blind spots, which can be an issue in a camera-based system.

Pressure images gathered from the pressure sensors are used to recognize different exercises and analyze the performance level of a subject while doing the exercises. An exercise monitoring system according to this disclosure supports continuous monitoring and quantification of pressure information. In this way, collected data may be used for objectively evaluating rehabilitation performance.

FIG. 1 illustrates an architecture for an exercise monitoring system, according to an embodiment of this disclosure. The system may be implemented for monitoring in a clinical setting, or for monitoring remotely, such as at a subject's home.

Referring to FIG. 1, the exercise monitoring system includes three main components: a textile sensor array 100 (e.g., an e-textile), a data sampling unit 102, and a processing unit 104. Textile sensor array 100 captures a two-dimensional pressure distribution of a subject as the subject lies on or otherwise applies force or pressure on texture sensor array 100, and data sampling unit 102 collects sensor outputs corresponding to the pressure distribution and conveys the sensor outputs to processing unit 104 via wireless or wired transmission. Processing unit 104 analyzes the sensor outputs for position and/or movement. Specifically, processing unit 104 executes or otherwise performs procedures described in the following sections.

Although textile sensor array 100, data sampling unit 102, and processing unit 104 are shown as separate components in FIG. 1, it is contemplated that these components can be combined or further sub-divided in other embodiments. It is also contemplated that processing performed by processing unit 104 also can be performed in whole or in part by another component, such as data sampling unit 102 or a remote server computer.

According to a specific implementation of the architecture of FIG. 1, a bed mattress incorporates a 2.5 m×1.25 m textile sensor array 100 of 64×32 pressure sensors. A differently dimensioned array area, or a different density of sensor array, may alternatively be used to gather more or less data.

Data sampling unit 102 is connected to textile sensor array 100 and performs matrix scanning to collect pressure image sequences. Retrieved pressure image signals from the pressure sensors are quantified to a digitized form, whose values range, for example, from 0 to 255, with 0 representing no pressure and 255 representing maximum pressure. Other digital resolutions may alternatively be used, such as a range of values from 0 to 511, or a range of values with offset such as −128 to +127, or other range suitable for the application.

Data sampling unit 102 interfaces with a data port of processing unit 104. Data is transferred serially or in parallel. For example, data may be transferred over a Universal Asynchronous Receiver/Transmitter ("UART") or Universal Serial Bus ("USB") port, or other standard or proprietary communication interface port. Data may be transferred by way of data packets. For example, for a system in which 64×32 sensors are used, every "0xA" data packet transmitted may represent a 64×32 frame of pressure sensor data. Sampling rate is selected based on the activity to be monitored, and may be adjusted as desired. Faster activity may require a higher sampling rate, whereas slower activity may use a lower sampling rate. In some embodiments, one sampling rate is selected and not adjusted during activity, whereas in other embodiments, sampling rate may be dynamically adjusted.

Textile sensor array 100 can be implemented using a textile sensor sheet that exhibits a piezoresistive effect, namely an electrical resistance of the sensor sheet varies in response to an applied force or pressure. In some embodiments, a textile sensor sheet can be implemented using textile fibers (e.g., synthetic or natural fibers) that are individually coated with an electrically conductive material, such as an electrically conductive polymer or a polymer with electrically conductive additives dispersed therein, and then knitted, woven, interlaced, bonded, or otherwise combined to form the sensor sheet. Examples of suitable electrically conductive polymers include nitrogen-containing aromatic polymers (e.g., polypyrroles, polycarbazoles, polyindoles, polyanilines, and polyazepines), sulfur-containing aromatic polymers (e.g., poly(3,4-ethylenedioxythiophene)), polythiophenes, polyfluorenes, polyphenylenes, polypyrenes, polyazulenes, polynapthalenes, polyacetylenes, and poly(p-phenylene vinylene). In other embodiments, a textile sensor sheet can be implemented using a pre-formed textile sheet, such as a woven or non-woven textile sheet, which is then coated, impregnated, or otherwise combined with an electrically conductive material to form the sensor sheet.

During use, an initial resistance between a top surface and a bottom surface of a textile sensor sheet can be high, as a natural structure of the sensor sheet can be a relatively loose collection of fibers that are spaced by air gaps. When force or pressure is applied to either, or both, of the surfaces of the sensor sheet, interior fibers can be pressed together, thereby lowering the resistance or increasing the conductance. Other implementations of a textile sensor sheet are contemplated, such as by leveraging a piezoelectric effect in place of, or in conjunction with, a piezoresistive effect. Textile sensor arrays are desirable for monitoring applications because of their flexibility, light weight, and cost-effectiveness.

Figure 2:
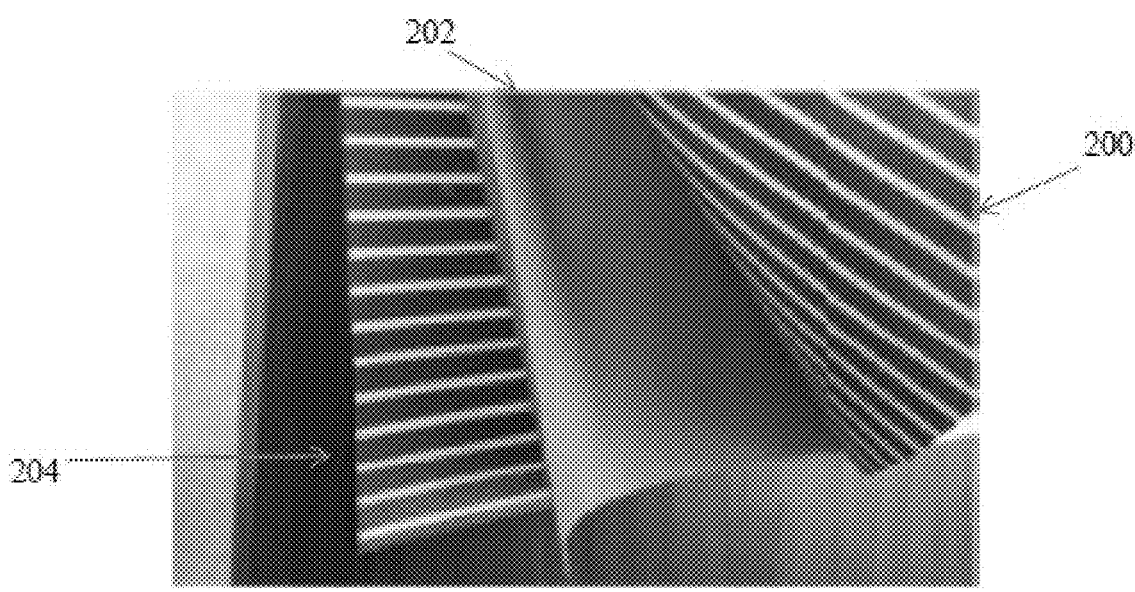
FIG. 2 shows an example of a pressure sensitive material.

FIG. 2 shows an example of a textile sensor array, according to an embodiment of this disclosure. The sensor array is implemented as a three layer, stacked structure, in which a middle layer 202 is a textile sensor sheet that is disposed between and laminated, bonded, or otherwise combined with a top layer 200 and a bottom layer 204. The textile sensor sheet may be but is not necessarily formed as a single sheet. In the illustrated embodiment, top layer 200 and bottom layer 204 can be implemented using woven or non-woven textile sheets that are coated with an electrically conductive material to form elongated conductive strips. Specifically, these elongated strips correspond to conductive buses that are substantially parallel to one another in the layer 200 and are substantially parallel to one another in bottom layer 204. Suitable electrically conductive materials include electrically conductive polymers, polymers with electrically conductive additives dispersed therein, metals, and metal alloys, and suitable coating techniques include deposition, spraying, printing, and roll-to-roll coating. As shown in FIG. 2, the conductive buses of top layer 200 are oriented relative to the conductive buses of bottom layer 204 so as to cross over one another at crossing points or intersections. In the illustrated embodiment, the conductive buses of top layer 200 are substantially orthogonal to the conductive buses of bottom layer 204, although other crossing angles are contemplated, such as from about 1° to about 90°, from about 5° to about 90°, from about 20° to about 90°, from about 45° to about 90°, from about 90° to about 179°, from about 90° to about 175°, from about 90° to about 160°, or from about 90° to about 135°.

Each intersection of a top conductive bus and a bottom conductive bus sandwiches a portion of the textile sensor sheet, thereby forming a pressure sensor at that location. In such manner, an array of pressure sensors is formed as an M×N matrix of pressure sensors, where M is a total number of the conductive buses of top layer 200, N is a total number of the conductive buses of bottom layer 204, and M×N is the total number of pressure sensors. In general, M can be the same as or different from N, and each of M and N can be 1 or more. To improve accuracy of position and/or movement detection, the sensor array desirably includes at least 25 pressure sensors, at least 50 pressure sensors, at least 100 pressure sensors, at least 500 pressure sensors, at least 1000 pressure sensors, at least 2000 pressure sensors, at least 3000 pressure sensors, at least 4000 pressure sensors, at least 5000 pressure sensors, at least 6000 pressure sensors, at least 7000 pressure sensors, or at least 8000 pressure sensors, and up to 10000 pressure sensors or more.

Figure 3:
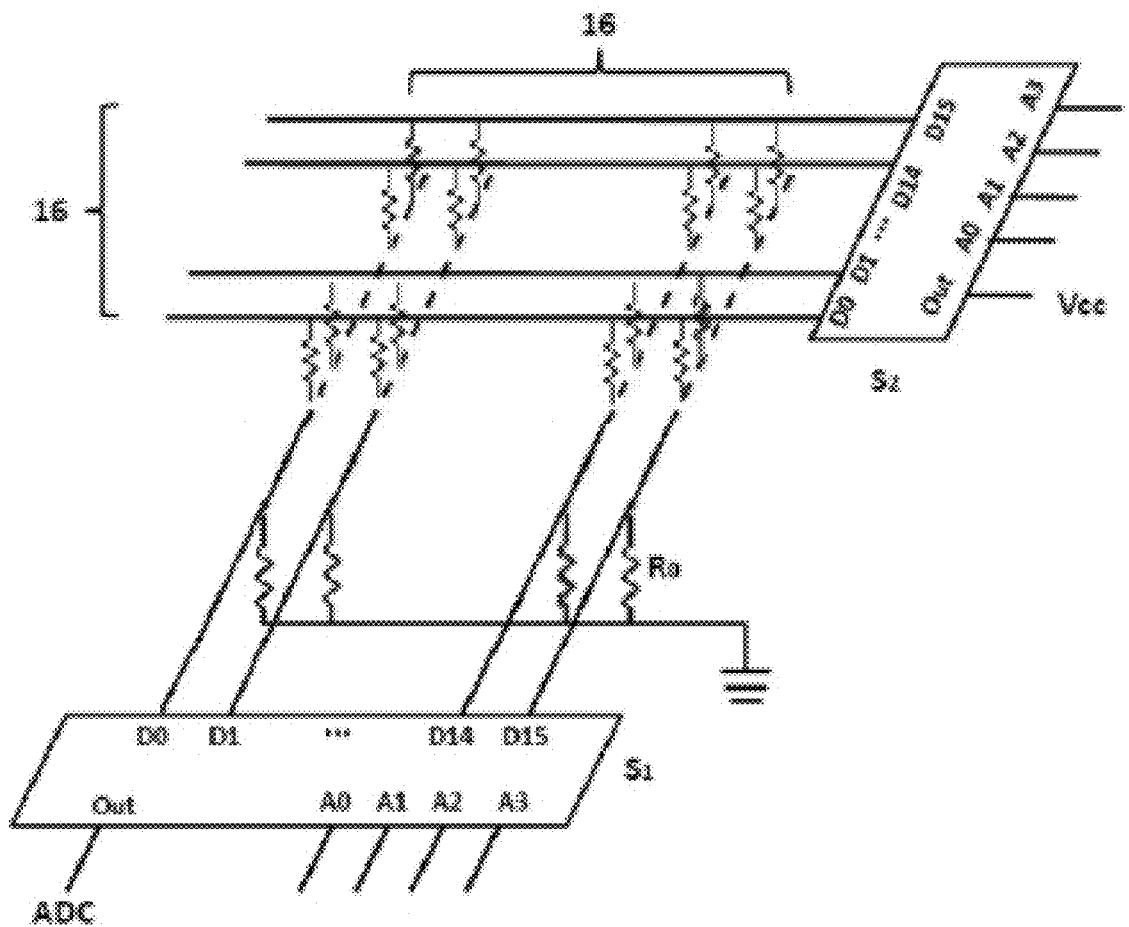
FIG. 3 is a schematic illustration of detecting pressure from a pressure sensitive material.

FIG. 3 shows a circuit for scanning a textile sensor array, which can be included in a data sampling unit in accordance with an embodiment of this disclosure. Each conductive bus on a bottom layer of the sensor array is connected to an analog-to-digital converter ("ADC") via an analog switch module $S_1$ and to ground via an offset resistor Ro. Each conductive bus on a top layer of the sensor array is connected to a voltage supply $V_{cc}$ via an analog switch module $S_2$. The analog switch modules $S_1$ and $S_2$ operate in conjunction to selectively address a particular pressure sensor, and a scanning sequence is synchronized by a microcontroller (not shown), which also can be included in the data sampling unit. For example, when $S_2$ connects a selected bus i on the top layer to $V_{cc}$ and $S_1$ connects a selected bus j to the ADC, the ADC can read a voltage through a pressure sensor located at an intersection of bus i and bus j, namely located at row i and column j, which voltage can be denoted as $V_{ij}$. In such manner, the circuit has random accessibility for reading an arbitrary sensor within the sensor array. Also, the single ADC can be shared among multiple sensors, thereby reducing manufacturing burden and facilitating large-scale sensing applications relative to alternative implementations in which each sensor has a separate ADC to sample a sensor output.

Figure 4:
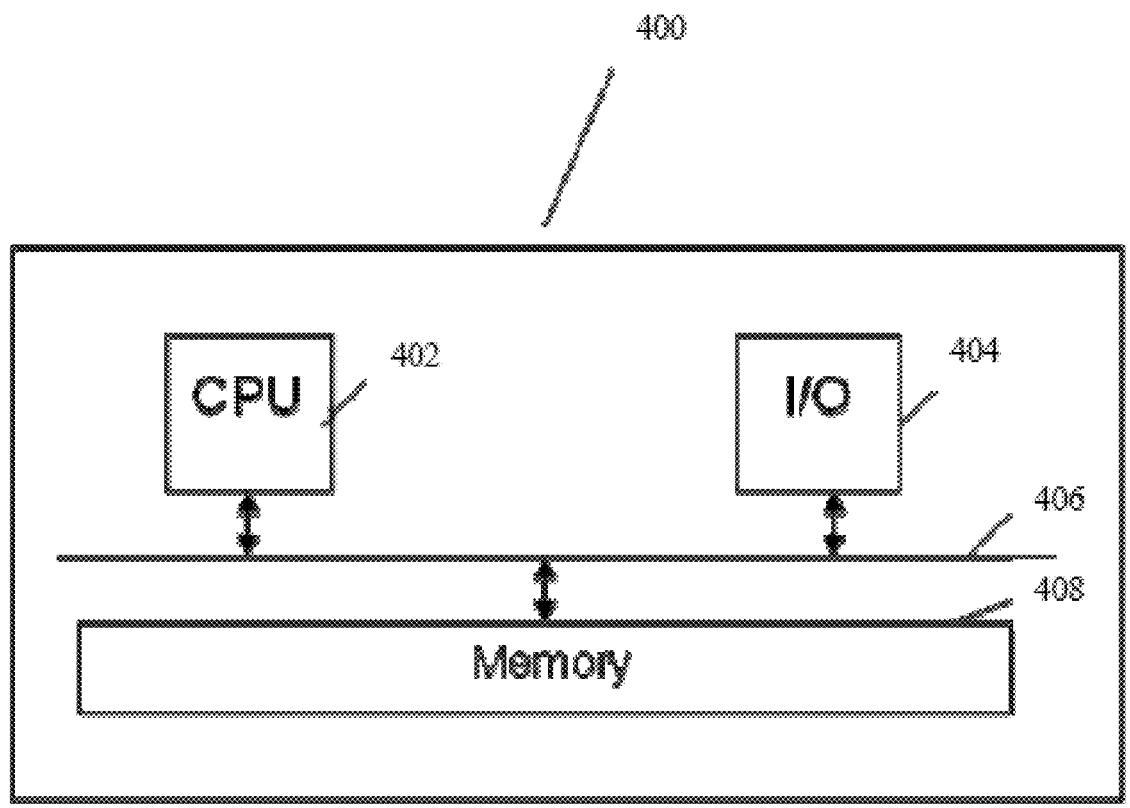
FIG. 4 illustrates an example of a computing device.

FIG. 4 shows a processing unit 400 implemented in accordance with an embodiment of this disclosure. Depending on a specific application, processing unit 400 can be implemented as, for example, a portable electronic device, a client computer, or a server computer. Referring to FIG. 4, processing unit 400 includes a central processing unit ("CPU") 402 that is connected to a bus 406. Input/Output ("I/O") devices 404 are also connected to bus 406, and can include a keyboard, mouse, display, and the like. An executable program, which includes a set of software modules for the procedures described in the following sections, is stored in a memory 408, which is also connected to bus 406. Memory 408 can also store a user interface module to generate alerts or visual presentations of position and/or movement. Processing unit 400 recognizes exercises and analyzes a subject's performance of the exercises and compliance to an exercise regimen. Processing unit 400 also can be referred to as an analysis device.

Exercise recognition uses a subject's pre-recorded training data to match present exercise data to known exercises. The training data includes samples of pressure image sequences captured during on-bed exercises, that are used to produce a low dimensional representation from the original high resolution pressure images. When new exercise data (i.e., pressure images) is recorded, it is mapped to the same low dimensional representation and matched to the closest exercise.

Figure 5:
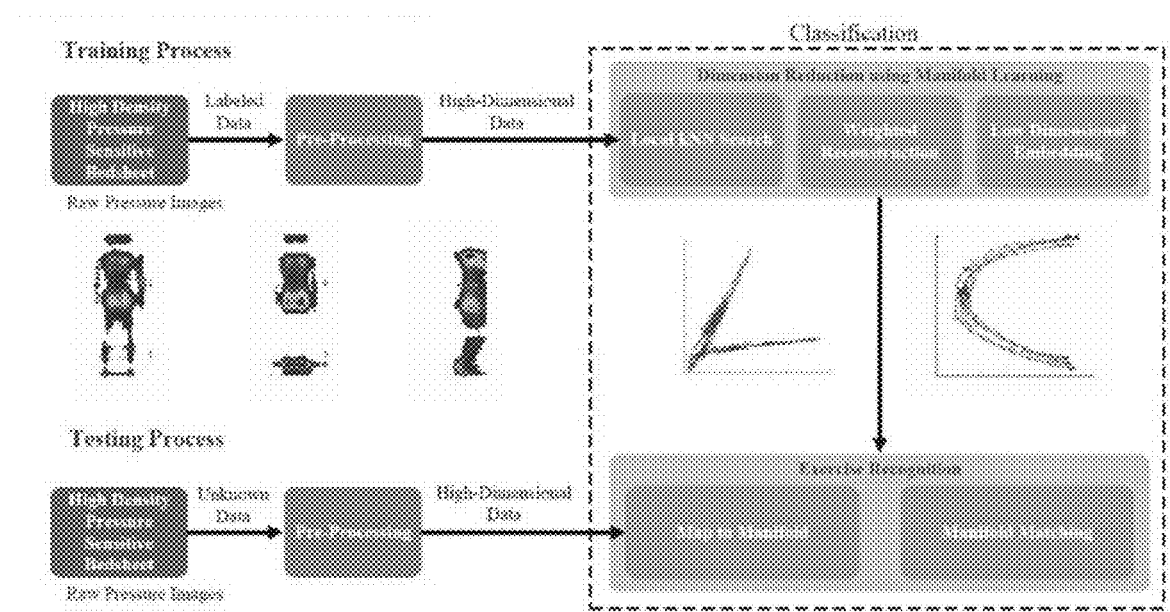
FIG. 5 is an overview of an example technique according to this disclosure.
Figures 6A, 6B:
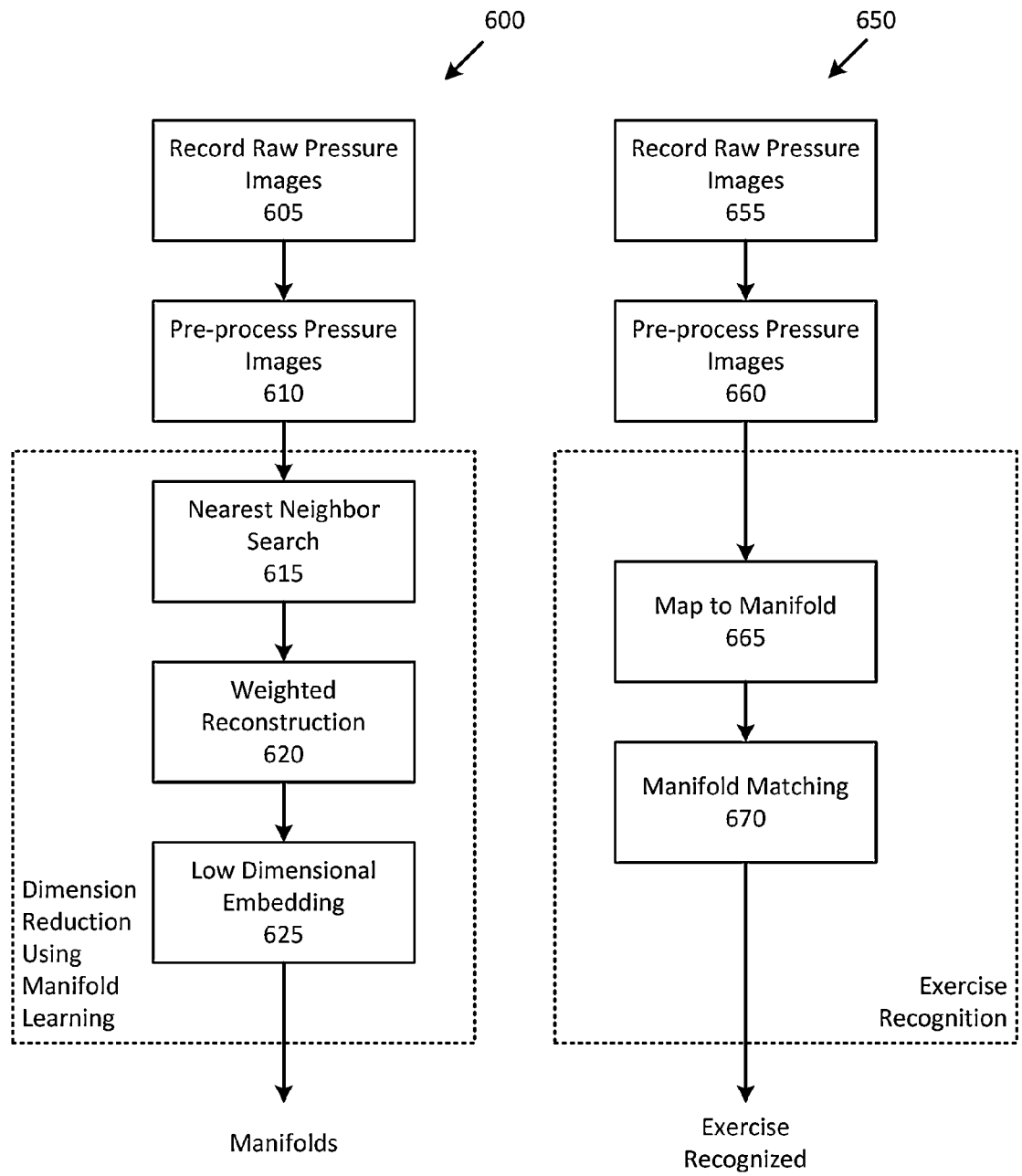
FIG. 6A is an example of a process for constructing manifolds from pressure data.
FIG. 6B is an example of a process of recognizing an exercise from pressure data.

FIG. 5 illustrates a summary of the training, classification, and testing process, provided as a visual introduction to the following discussion of FIGS. 6A and 6B.

FIG. 6A illustrates a process 600 for using a sequence of pressure images acquired during a subject's exercise as training data to learn manifolds representing various exercises. FIG. 6B illustrates a process 650 for matching a sequence of pressure images acquired during a subject's exercise to an exercise manifold so as to identify and evaluate the subject's movements. Both processes 600 and 650 begin in the same way—to record a sequence of raw pressure images (blocks 605, 655) and to pre-process the raw pressure images (blocks 610, 660).

Recording the raw pressure images (blocks 605, 655) is described above with respect to FIGS. 1-4.

Pre-processing of the raw pressure images (blocks 610, 660) allows for standardization of the pressure images. For example, because a subject may be located anywhere on the bed sheet, the recorded pressure images are aligned to a common center of mass and centered in the image space during pre-processing. A smoothing filter of a symmetric 5×5 unit normal distribution is applied to reduce the effects of noise. The pressure images are also normalized so that the sum of pixel weights is one, to account for differences in body mass between subjects, or between pressure images of a subject taken at different times. Thus, blocks 610/660 provide pre-processed images in a standardized and normalized form, with reduced noise. Examples of images at least partially pre-processed are provided in FIGS. 7A-11.

Returning to training process 600 in FIG. 6A, following pre-processing (block 610), sequences of pressure images are transformed into low-dimensional data manifolds in a three-stage process (blocks 615, 620, 625). A pressure image sequence X is mapped to a low dimensional space based on a Local Linear Embedding (LLE) framework, which has various applications in machine learning systems. LLE is an unsupervised technique that reconstructs global data non-linearly while preserving local linearity. After the LLE computation, similar pressure images will be clustered within the low dimensional manifold. Other dimensionality reduction procedures can be used, such as those based on Sammon's mapping, principal component analysis, Laplacian eigenmaps, and so forth.

At block 615, a search is performed for the k-nearest neighbors (KNN) for each image. In the searching process, a Euclidean distance is used to evaluate the similarity between images. One way to determine group size k in the searching procedure is to use a fixed integer, and another way is to identify the neighborhood by a threshold value in distance metrics. In either case, any image within a given distance will be recognized as a neighbor. Normally the topology of embedding will be well-preserved over a range of neighborhood sizes. In the examples provided later (related to Table 1), the search value k was thirty, such that the search was to find the thirty nearest neighbors of each pressure image.

At block 620, a sample image is reconstructed using the sample's nearest neighbors: an arbitrary image x has k-nearest neighbors $x_i$, and x can ideally be represented as a linear combination of its neighbors $x_i$. In general, an exact reconstruction will not be found, so a reconstruction error e can be formulated as in equation (1), where $w_i$ denotes the reconstruction weight for the neighbor $x_i$.

$$e = \left\| x - \sum_{i=1}^{k} w_i x_i \right\| \tag{1}$$

An optimization process minimizes the reconstruction error of the images by setting the weight $w_i$ values. There are two attributes of the problem to ensure it is well-imposed: (a) exclusiveness—the weight $w_i$ of x is zero if $x_i$ is not in the nearest neighbor list of x; (b) normalization—the sum of the weights of nearest neighbors should be equal to one. Therefore, the problem for the images is as in equation (2).

$$E = \sum_{j=1}^{N} \left\| x_j - \sum_{i=1}^{N} w_{ij} x_{ij} \right\| \tag{2}$$

Equation (2) represents the reconstruction problem and has a closed least square solution, where the weights $w_{ij}$ can be solved efficiently.

At block 625, an embedding in a low dimensional space is constructed. The intrinsic geometrical structure of each local cluster is characterized by $w_{ij}$, and the neighborhood relation in high dimensional space should be preserved in low dimensional space (i.e., within a manifold). The embedding process searches for the low dimensional representation y of x by minimizing an error E' shown in equation (3), where $y_j$ are the corresponding points in the low dimensional manifold.

$$E' = \sum_{j=1}^{N} \left\| y_j - \sum_{i=1}^{N} w_{ij} y_{ij} \right\| \quad (3)$$

Equation (3) is in a quadratic form and the embedding optimization process is efficiently solvable. Additionally, the manifold points $y_i$ will be computed globally and simultaneously, and no local optima will affect the construction result.

Equation (2) indicates that the low dimensional construction is based on the locality of the high dimension data. This means that the computed manifold $y_i$ can be translated with an arbitrary displacement without affecting the equation.

LLE provides that the computed manifold $y_i$ can be rotated by an arbitrary angle without affecting equation (3). This geometric attribute can be represented as shown in equations (4) and (5).

$$\sum_{i=1}^{N} y_i = 0 \quad (4)$$

$$\frac{1}{N} \sum_{i=1}^{N} y_i \cdot y_i = 1 \quad (5)$$

Therefore, the manifold construction problem becomes an eigenvalue problem, in which the matrix rank is selected to have the desired manifold dimension.

Once the training image sequence has been reduced in dimensionality to its corresponding low dimensional form, the manifolds may be used to identify and analyze exercises from new image sequences received.

Returning to FIG. 6B, process 650 maps (block 665) the pre-processed images from block 660 to a manifold, and matches the manifold to one of the manifolds determined using training images in process 600. Note that it is possible to run the entire LLE process again on the combined new images and training images in order to find the low dimensional representation of the new images. However, as this could take significant processing time and resources, alternatively a portion of the process may be executed. To find the low dimensional representation $\hat{y}$ of a new image $\hat{x}$, the weights $w_i$ are computed from the k nearest neighbors of $\hat{x}$ in the training set, $x_i$. It is a least squares solution to minimize equation (6) with the restraint of equation (7).

$$\left\| \hat{x} - \sum_{i=1}^{k} w_i x_i \right\| \quad (6)$$

$$\sum_{i=1}^{k} w_i = 1 \quad (7)$$

Since the corresponding low dimensional co-ordinates of $x_i$ are known during the training phase, the resultant embedded co-ordinates for $\hat{y}$ may be constructed using the same weights, as shown in equation (8), where $y_i$ are the corresponding embedded points of $x_i$.

$$\hat{y} = \sum_{i=1}^{k} w_i y_i \quad (8)$$

After the new pressure image sequence is mapped to a manifold (block 665), the new manifold may be matched (block 670) to a known manifold (e.g., from the training image sequences). The new manifold is checked to see how well it follows the trajectory of a known exercise manifold. Trajectories are compared using a similar idea to the Hausdorff distance. The distance of a point to a manifold is equal to the shortest Euclidean distance to any point in the manifold. The similarity of two manifolds is the mean of the point distances of the points of one manifold, M1, to the other manifold, M2. This idea is shown in equation (9), where $T_{M1}$ and $T_{M2}$ are the number of points in each manifold.

$$s(M_1, M_2) = \frac{1}{T_{M_1}} \sum_{i=1}^{T_{M_1}} \min_{1 \leq j \leq T_{M_2}} \| M_1(i) - M_2(j) \| \quad (9)$$

This metric allows manifolds of different lengths to be compared, as different subjects take different times to perform each activity.

The Hausdorff metric is not symmetric, and the sum in equation (10) is used as a manifold matching metric.

$$d(M_1, M_2) = s(M_1, M_2) + s(M_2, M_1) \quad (10)$$

Thus, to measure how well a subject adheres to a prescribed exercise, the new exercise manifold may be measured against the expected exercise manifold.

The exercise monitoring technique described above was evaluated on ten subjects: seven male subjects and three female subjects. The weight of the subjects ranged from 50 kg to 85 kg, and height of the subjects ranged from 155 cm to 188 cm. Five on-bed exercises were performed: alternating leg-lifts, head-lifts, alternating heel slides, alternating lateral rolls (lying on back to lying on side), and sit-ups. One recorded image sequence represented one exercise activity (e.g. one leg lift exercise activity including lifting of the right leg followed by lifting of the left leg). Each image sequence included at least 40 individual images. In the training data collection, at least five sets of image sequences were recorded for each of the five on-bed exercises for each subject. The training data for each subject was combined, and manifold learning was applied to generate the training manifolds for the exercises.

The system used in the evaluation included a 64×128 pressure sensor array, a data sampling unit, and a tablet computer for data analysis and storage. The sensor array is based on e-textile material which is fiber-based yarn coated with piezoelectric polymer. The bed sheet is a three-layer sandwiched structure. The top layer is fabric coated with 64 parallel conductive lines. The middle layer is the e-textile material and the bottom layer has 128 conductive lines arranged perpendicular to the top 64 lines. At each intersection of conductive lines, the structure forms a pressure sensitive resistor. There are effectively 8192 pressure sensors in the 64×128 pressure sensor array.

Recognition results of the evaluation are provided in the confusion matrix of Table 1.

TABLE 1

|  | Leg Lift | Head Lift | Heel Slide | Lateral Roll | Sit-Up | Total | Recall |
|---|---|---|---|---|---|---|---|
| Leg Lift | 38 | 3 | 5 | 0 | 0 | 46 | 82.6% |
| Head Lift | 8 | 39 | 2 | 0 | 0 | 49 | 79.6% |
| Heel Slide | 7 | 0 | 54 | 0 | 0 | 61 | 88.5% |
| Lateral Roll | 0 | 0 | 0 | 44 | 0 | 44 | 100% |
| Sit-Up | 0 | 0 | 0 | 1 | 56 | 57 | 98.2% |
| Total | 53 | 42 | 61 | 45 | 56 | 257 | |
| Precision | 71.7% | 92.9% | 88.5% | 97.8% | 100% | | |

As seen in Table 1, the highest recognition rates for the exercises tested were Lateral Rolls and Sit-Ups, as may be expected, since these exercises involve the greatest physical exertion and hence the greatest pressure image differences.

FIGS. 7A-11 are examples of pre-processed pressure images, illustrating the resolution achieved using the pressure-sensitive bed sheet. In each of FIGS. 7A-11, three or four pressure images are shown in sequence. More pressure images may be captured during an exercise for better analysis.

Figure 7A:
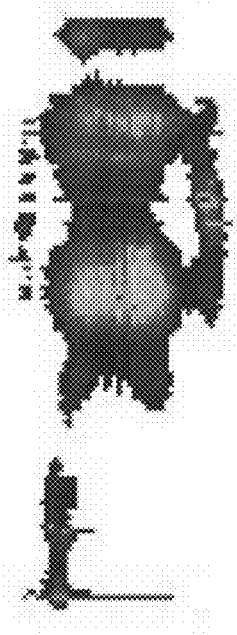
FIGS. 7A-7C are a sequence of pressure images captured during a leg lift exercise.
Figure 7B:
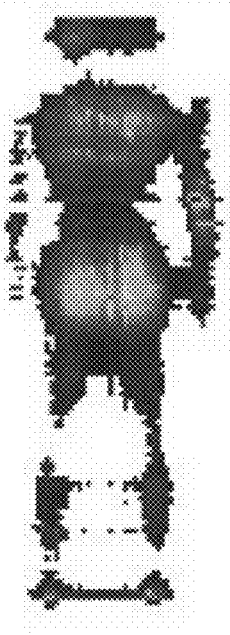
Figure 7C:
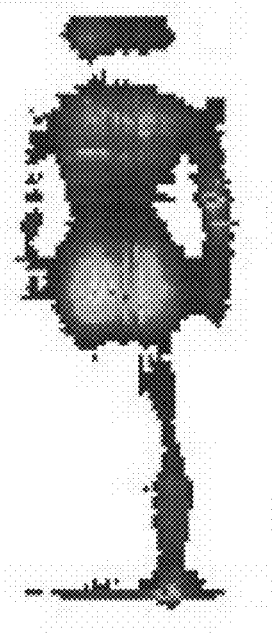

FIGS. 7A-7C show a sequence of three pressure images captured during a leg lift exercise. FIG. 7A shows a first leg lifted and the second leg down, FIG. 7B shows the first leg and the second leg down, and FIG. 7C shows the first leg down and the second leg lifted.

Figure 8A:
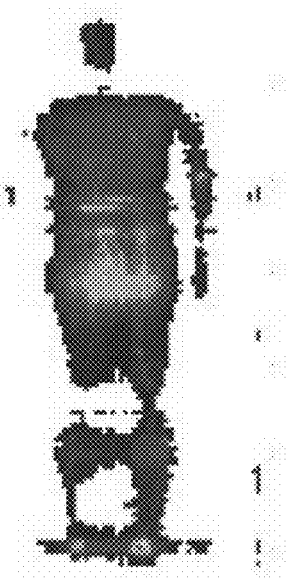
FIGS. 8A-8C are a sequence of pressure images captured during a head lift exercise.
Figure 8B:
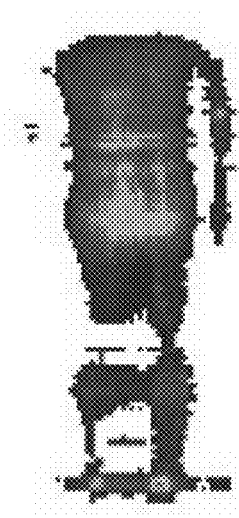
Figure 8C:
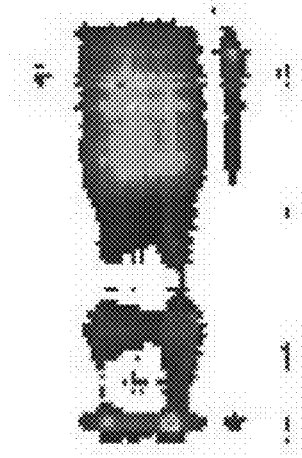

FIGS. 8A-8C show a sequence of three pressure images captured during a head lift exercise. FIG. 8A shows the head down, FIG. 8B shows the head lifted, and FIG. 8C shows the head and shoulders lifted.

Figure 9A:
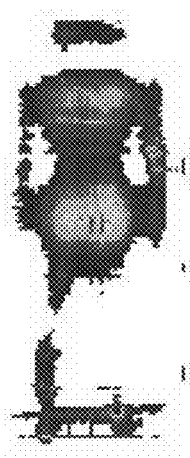
FIGS. 9A-9D are a sequence of pressure images captured during a heel slide exercise.
Figure 9B:
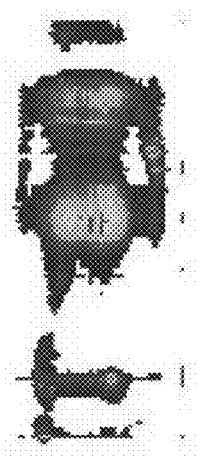
Figure 9C:
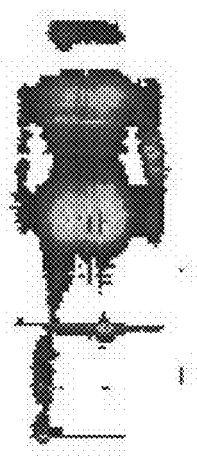
Figure 9D:
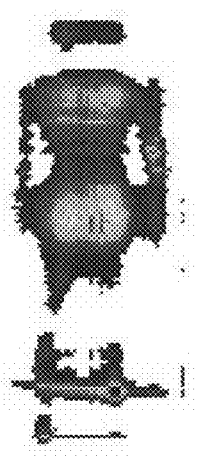

FIGS. 9A-9D show a sequence of four pressure images captured during a heel slide exercise, where one leg remains down throughout the exercise, and the heel of the foot of the other leg is slid along the bed as the knee is bent and unbent. FIG. 9A shows the heel of one foot with the associated moving leg nearly extended, FIGS. 9B and 9C show the heel as the leg is progressively bent and the heel slid along the bed sheet, and FIG. 9D shows the heel as the leg is straightened and the heel slid back along the bed sheet towards a leg-extended position.

Figure 10:
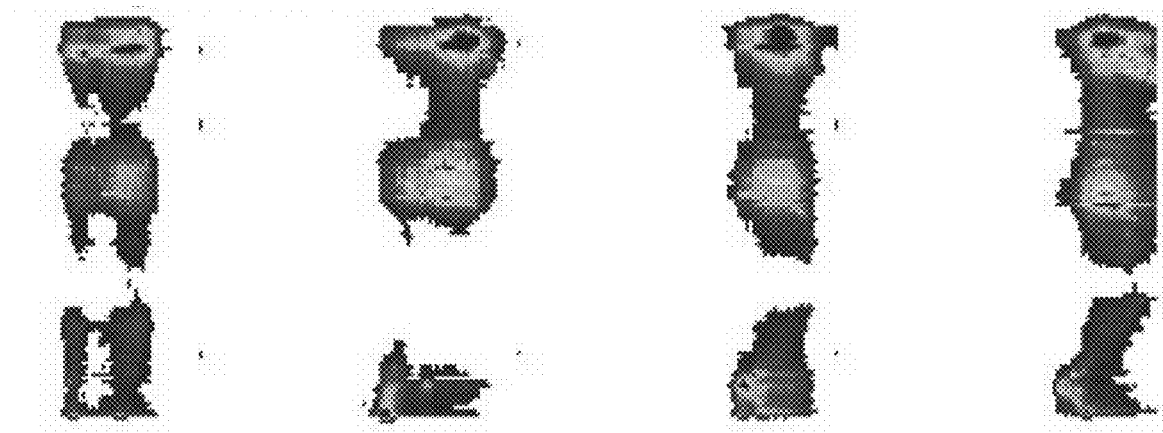
FIG. 10 is a sequence of pressure images captured during a lateral roll exercise.

FIG. 10 shows a sequence of four pressure images captured during a subject's lateral roll.

Figure 11:
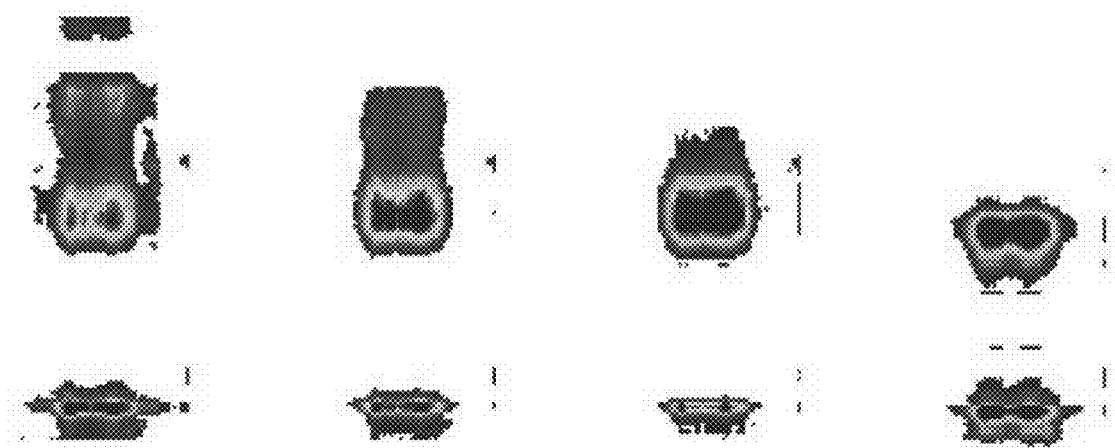
FIG. 11 is a sequence of pressure images captured during a sit-up exercise.

FIG. 11 shows a sequence of four pressure images captured during a sit-up, from a torso-flat position to a sitting position.

Figure 12A:
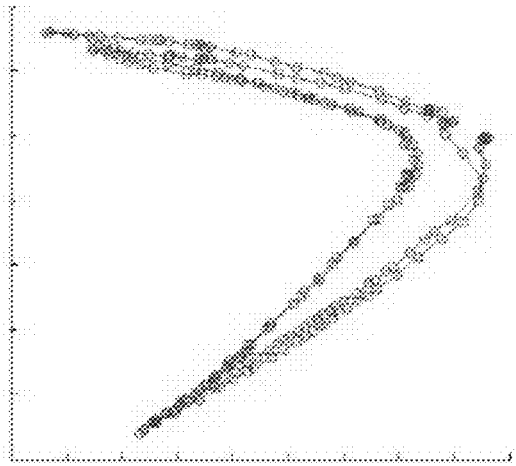
FIG. 12A is a manifold constructed for a leg lift exercise.
Figure 12B:
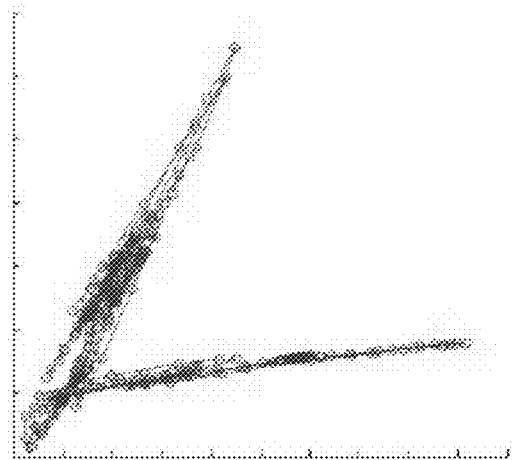
FIG. 12B is a manifold constructed for a heel slide exercise.
Figure 12C:
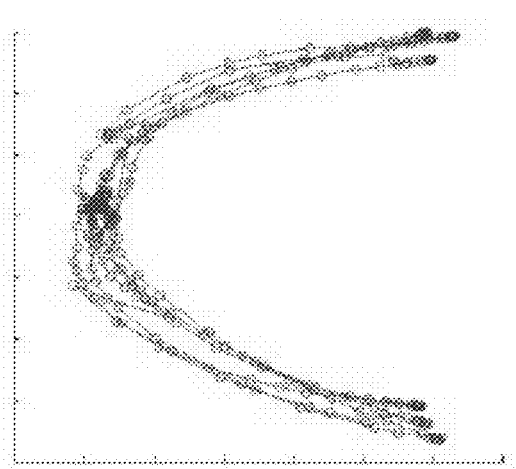
FIG. 12C is a manifold constructed for a lateral roll exercise.
Figure 12D:
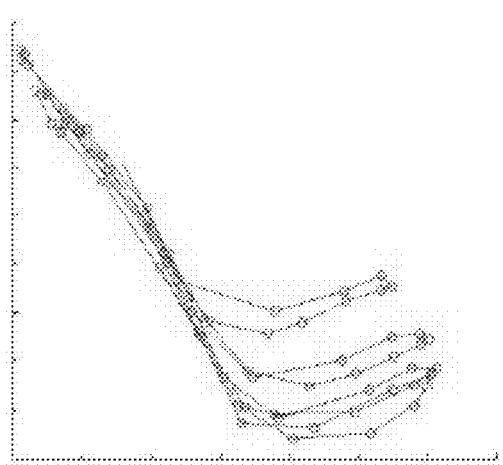
FIG. 12D is a manifold constructed for a sit-up exercise.

FIGS. 12A-12D illustrate examples of how the pressure images may be represented by low dimensional (namely, two-dimensional) visualization of manifolds. The axes shown in FIGS. 12A-12D are calculated by the LLE technique as a best way to represent the manifold structure. Each point represents an image that has been transformed into the two dimensional space. Each curve (i.e., manifold) represents a sequence of images, and the trajectory of the curve represents the associated exercise sequence. FIG. 12A provides examples of leg lift manifolds, FIG. 12B provides examples of heel slide manifolds, FIG. 12C provides examples of lateral roll manifolds, and FIG. 12C provides examples of sit-up manifolds.

The dimension reduction technique specifies the data to be non-sparse, so there should be a sufficient number of pressure images to track motion. For example, pressure images may be captured at a rate of 2-5 images per second. Higher sampling rates may also be used. At high sampling rates, there may be a tradeoff in image resolution, depending on the available computing resources.

Instructions may be provided to subjects to direct an exercise session, such as a physical therapy session. For example, instruction may be provided by way of treatment scripts presented by a computing device such as a tablet or smart phone or other computing device, where the treatment scripts are stored in the computing device and played on demand by the subject. A treatment script may present instructions by way of text or aurally. In some embodiments, a treatment script is accompanied by monitoring requirements, and if the subject does not attain the requirements, the discrepancy may be logged or a warning displayed or sounded, such as by text, speech, alarm, display of lights, or display of a representation of the goal to be achieved. One monitoring requirement may be, for example, that when the subject is instructed to lift a knee, that the knee is lifted by more thirty degrees from the surface that includes the textile sensitive array. The system infers such movement by analyzing the pressure image sequences.

Lifting speed of a limb, frequency of repetition, and duration of a movement, for example, can also be determined by reading and analyzing the pressure images.

Raw data, pressure images, manifolds, and analyses may be reviewed remotely, allowing a caregiver to monitor a subject's actions and progress.

Although illustrated with respect to a flat surface such as a bed, the system may also be used for other applications, such as in chairs, wheelchairs, vehicle seats, and inclined surfaces.

An embodiment of this disclosure relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and procedures described herein. The media and computer code may be those specially designed and constructed for the purposes of this disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM memory devices. Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of this disclosure may be downloaded as a computer program product, which may be transferred from a remote computer (e.g., a server computer) to a requesting computer (e.g., a client computer or a different server computer) via a transmission channel. Another embodiment of this disclosure may be implemented in hardwired circuitry in place of, or in combination with, machine-executable software instructions.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, operation or operations, to the objective, spirit and scope of the invention. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

What is claimed is:

1. A system, comprising:
   a pressure sensitive material that provides an indication of applied pressure for a plurality of locations on the material; and
   a non-transitory computer-readable storage medium for a processing device in communication with the pressure sensitive material, including instructions to:
      receive the indication of applied pressure;
      determine, for each of a plurality of measurement periods, a pressure image from the indication of applied pressure such that a sequence of pressure images is determined; and
      construct a manifold representing the sequence of pressure images.

2. The system of claim 1, wherein the pressure sensitive material comprises an e-textile material layer.

3. The system of claim 1, wherein the pressure sensitive material is constructed in multiple layers, including at least: a first layer including conductive traces, a second layer of variable conductivity material positioned next to the first layer, and a third layer including conductive traces positioned next to the second layer.

4. The system of claim 3, wherein the plurality of locations on the material is a plurality of intersections of the conductive traces of the first layer and the third layer, and at each intersection, the conductive traces of the first layer and the third layer cross at an angle with respect to each other, and the conductive traces of the first layer and the third layer are separately selectable to allow for measuring a conductance at each intersection.

5. The system of claim 4, wherein the indication of applied pressure includes the conductance measured at multiple intersections.

6. The system of claim 1, wherein the instructions to construct the manifold include instructions to:
   search for the k nearest neighbors;
   perform a weighted reconstruction; and
   create a low dimensional embedding.

7. The system of claim 1, wherein the indication of applied pressure represents training data and the manifold is a first manifold, and the analysis device is further configured to:
   determine the similarity of a second manifold to the first manifold.

8. The system of claim 1, wherein the manifold represents a defined rehabilitation exercise.

9. The system of claim 8, wherein the defined rehabilitation exercise is one of:
   leg lift, heel slide, lateral roll, head lift, and sit-up.

10. A method, comprising:
    receiving data representing conductance measurements from a plurality of pressure sensors;
    determining a sequence of pressure maps from at least a portion of the data;
    for each pressure map in the sequence of pressure maps, searching for the k nearest neighbors;
    performing a weighted reconstruction from the k nearest neighbors; and
    creating a low dimensional embedding of the weighted reconstruction.

11. The method of claim 10, wherein the low dimensional embedding is embedding in a manifold.

12. The method of claim 10, wherein the data represents pressure between a subject and a surface measured at a plurality of points on the surface, and the low dimensional embedding represents a defined exercise performed by the subject on the surface.

13. The method of claim 12, further comprising:
    comparing the low dimensional embedding to a previously-created low dimensional embedding to identify the exercise.

14. The method of claim 13, further comprising:
    determining a difference between an actual performance of the exercise and an expected performance of the exercise by way of the comparing.

15. The method of claim 10, wherein the sequence of pressure maps is a first sequence, further comprising instructions for determining a plurality of sequences of pressure maps including the first sequence, and creating a low dimensional embedding based on the plurality of sequences of pressure maps.

16. A non-transitory computer-readable storage medium, comprising instructions for:
    determining at least one sequence of pressure maps from data representing pressure between an object and a surface measured at a plurality of times during an interval;
    pre-processing each pressure map of the at least one sequence of pressure maps, thereby generating at least one sequence of standardized and normalized pressure maps; and
    performing dimension reduction on the at least one sequence of standardized and normalized pressure maps using manifold learning.

17. The non-transitory computer-readable storage medium of claim 16, wherein the dimension reduction results in the construction of a manifold representing a sequence of movements of the object.

18. The non-transitory computer-readable storage medium of claim 16, wherein the dimension reduction results in the construction of a manifold representing an expected sequence of movements.

19. The non-transitory computer-readable storage medium of claim 18, wherein the manifold representing the expected sequence of movements represents an expected performance of an exercise, further comprising instructions for comparing the manifold representing the expected sequence of movements to a manifold representing an actual sequence of movements to identify whether the actual sequence of movements represents a performance of the exercise.

20. The non-transitory computer-readable storage medium of claim 16, wherein the manifold representing the sequence of movements is a first manifold and represents a record of performance of an exercise, further comprising instructions for comparing the first manifold to a second manifold to determine progress in performance of the exercise.

* * * * *